US009366611B2

(12) United States Patent
Jung

(10) Patent No.: US 9,366,611 B2
(45) Date of Patent: Jun. 14, 2016

(54) APPARATUS FOR MAPPING LINER WEAR OF A BEARING

(71) Applicant: Noah Jung, California, MD (US)

(72) Inventor: Noah Jung, California, MD (US)

(73) Assignee: The United States of America as represented by the Secretary at the Navy, Washington, DC (US)

( * ) Notice: Subject to any disclaimer, the term of this patent is extended or adjusted under 35 U.S.C. 154(b) by 160 days.

(21) Appl. No.: 14/496,736

(22) Filed: Sep. 25, 2014

(65) Prior Publication Data

US 2016/0091403 A1 Mar. 31, 2016

(51) Int. Cl.
*G01N 3/56* (2006.01)
*F16C 41/00* (2006.01)
*G01M 13/04* (2006.01)

(52) U.S. Cl.
CPC .............. *G01N 3/56* (2013.01); *F16C 41/007* (2013.01); *G01M 13/04* (2013.01); *F16C 2233/00* (2013.01); *G01N 2203/0033* (2013.01)

(58) Field of Classification Search
CPC . G01N 3/56; G01N 2203/0033; G01N 19/02; G01M 13/04; F16C 11/0614; F16C 11/0695; F16C 41/007; F16C 2233/00
USPC .......................................................... 73/7, 9
See application file for complete search history.

(56) References Cited

U.S. PATENT DOCUMENTS

| 3,201,996 | A | * | 8/1965 | Silvia ..................... | G01M 13/04 73/593 |
| 4,644,261 | A | * | 2/1987 | Carter .................... | G01B 7/312 324/662 |
| 4,941,105 | A | * | 7/1990 | Marangoni ........... | G01M 13/04 702/42 |
| 5,133,211 | A | * | 7/1992 | Brown ................... | G01M 13/04 73/115.07 |
| 5,226,308 | A | * | 7/1993 | Gibson .................. | G01M 13/04 73/9 |
| 5,889,218 | A | * | 3/1999 | Sato ....................... | G01M 13/04 73/593 |

\* cited by examiner

*Primary Examiner* — Justin Olamit
(74) *Attorney, Agent, or Firm* — Mark O. Glut; NAWCAD

(57) ABSTRACT

An apparatus for mapping liner wear of a bearing around the circumference of the bearing which includes a rotary indexer that can hold the bearing, a shaft, a force applying mechanism, a rotating mechanism, a digital displacement indicator, and a recorder.

1 Claim, 5 Drawing Sheets

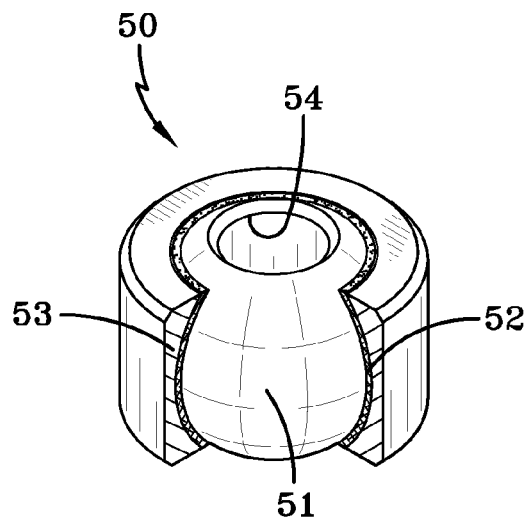
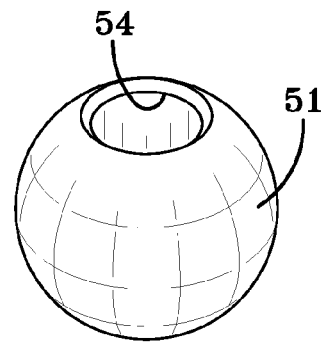
FIG-2A    FIG-2B
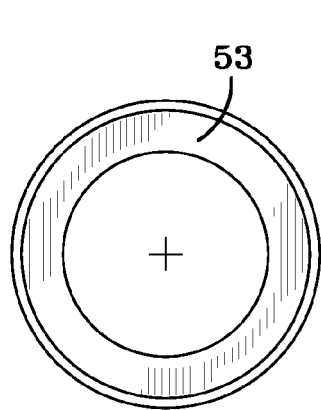
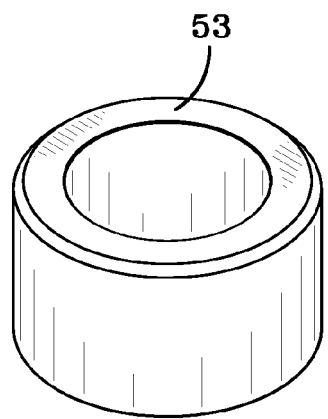
FIG-2C    FIG-2D

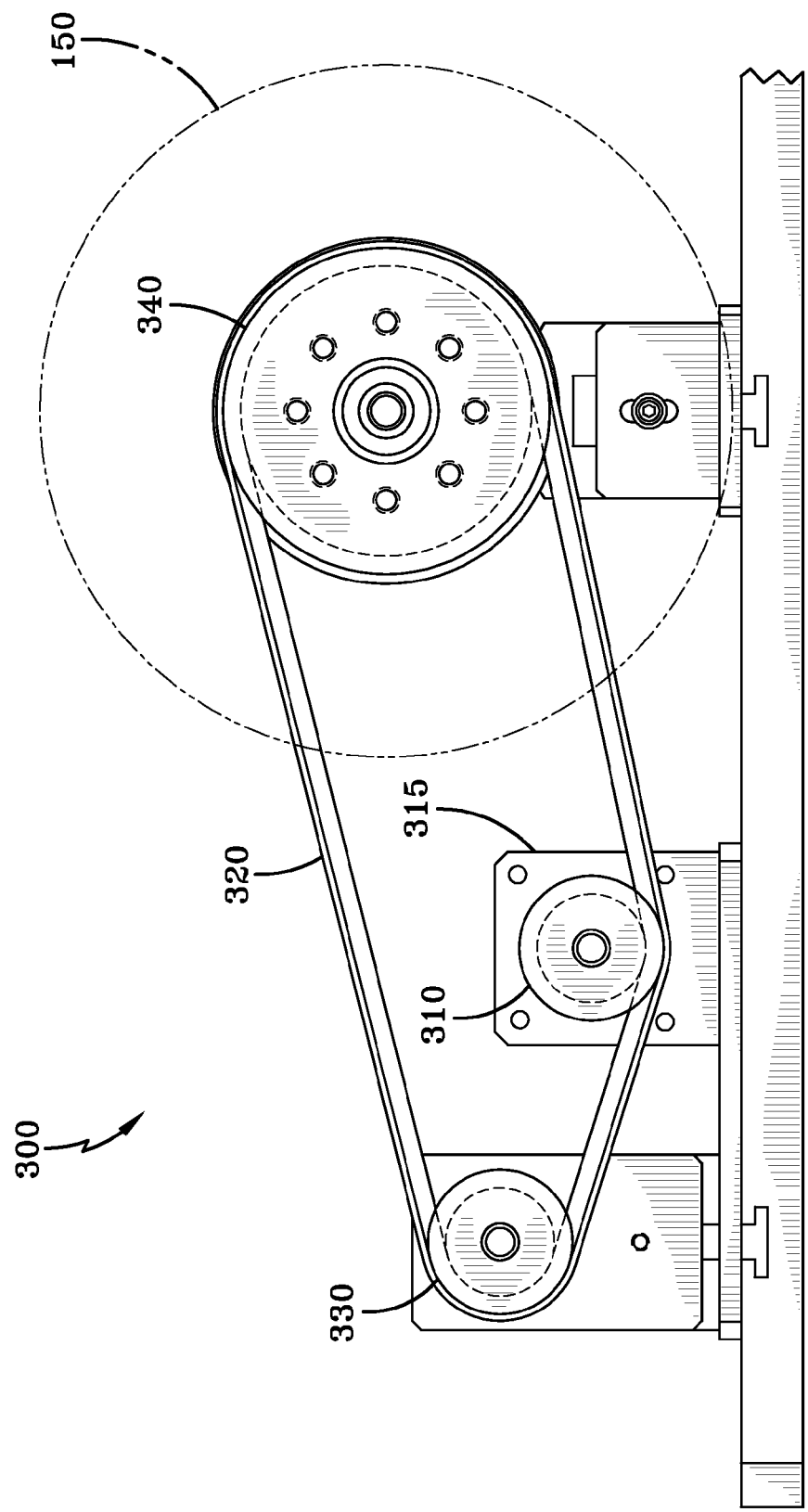

APPARATUS FOR MAPPING LINER WEAR OF A BEARING

STATEMENT OF GOVERNMENT INTEREST

The invention described herein may be manufactured and used by or for the Government of the United States of America for governmental purposes without payment of any royalties thereon or therefore.

BACKGROUND

Liner wear in a bearing is the primary metric used to determine usable life in lined bearings. Therefore, it is very important to quantify the amount of wear on a bearing liner. A liner on or for a bearing can be described, but without limitation, as a sacrificial wear surface applied circumferentially to a bearing. Measuring liner wear around the entire bearing circumference helps to better quantify the maximum wear being experienced. This helps determine if liner systems do in fact meet certain wear thresholds.

Bearings, especially in the military, are sometimes used in environments that include contamination and vibrations that may introduce unusual wear patterns. If these bearings are used in critical applications, it is very important to accurately analyze bearing liner wear to predict usable life. A liner wear map around the entire bearing circumference may help identify premature failure by identifying features such as secondary wear zones or wear not in the region of the expected loading.

SUMMARY

The present invention is directed to an apparatus for mapping liner wear of a bearing that meets the needs enumerated above and below.

The present invention is directed to an apparatus for mapping liner wear of a bearing around the circumference of the bearing which includes a rotary indexer that can hold the bearing, a shaft, a force applying mechanism, a rotating mechanism, a digital displacement indicator, and a recorder.

It is a feature of the invention to provide an apparatus for mapping liner wear of a bearing around the circumference of the bearing for use with lined bearings which are utilized in components found on aircraft and in similar systems.

It is a feature of the invention to provide that an apparatus for mapping liner wear of a bearing around the circumference of the bearing which accurately analyzes bearing wear, is able to interpret usable bearing life, and provides a map of liner wear around the entire bearing circumference.

It is a feature of the present invention to provide an apparatus for mapping liner wear of a bearing around the circumference of the bearing that helps provide detailed information regarding premature bearing liner failures.

It is a feature of the present invention to provide a means of nondestructively locating features of interest inside of a lined bearing.

DRAWINGS

These and other features, aspects and advantages of the present invention will become better understood with reference to the following description and appended claims, and accompanying drawings wherein FIG. 1 is an expanded perspective view of the apparatus for mapping liner wear of a bearing;

FIG. 2a is a perspective view of the bearing;

FIG. 2b is a perspective view of the ball;

FIG. 2c is top view of the outer ring;

FIG. 2d is a perspective view of the outer ring;

Figure 3:
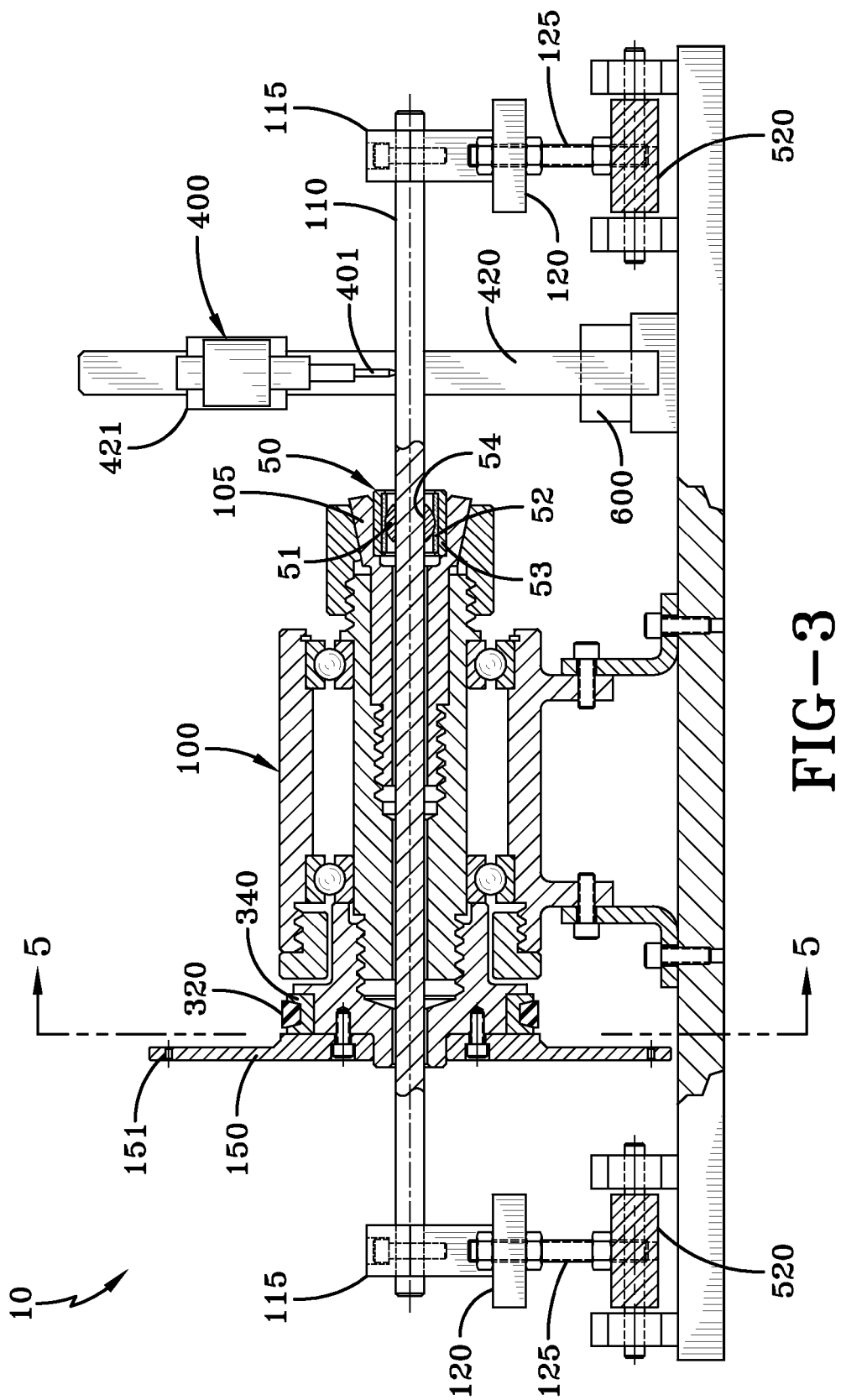
Figure 4:
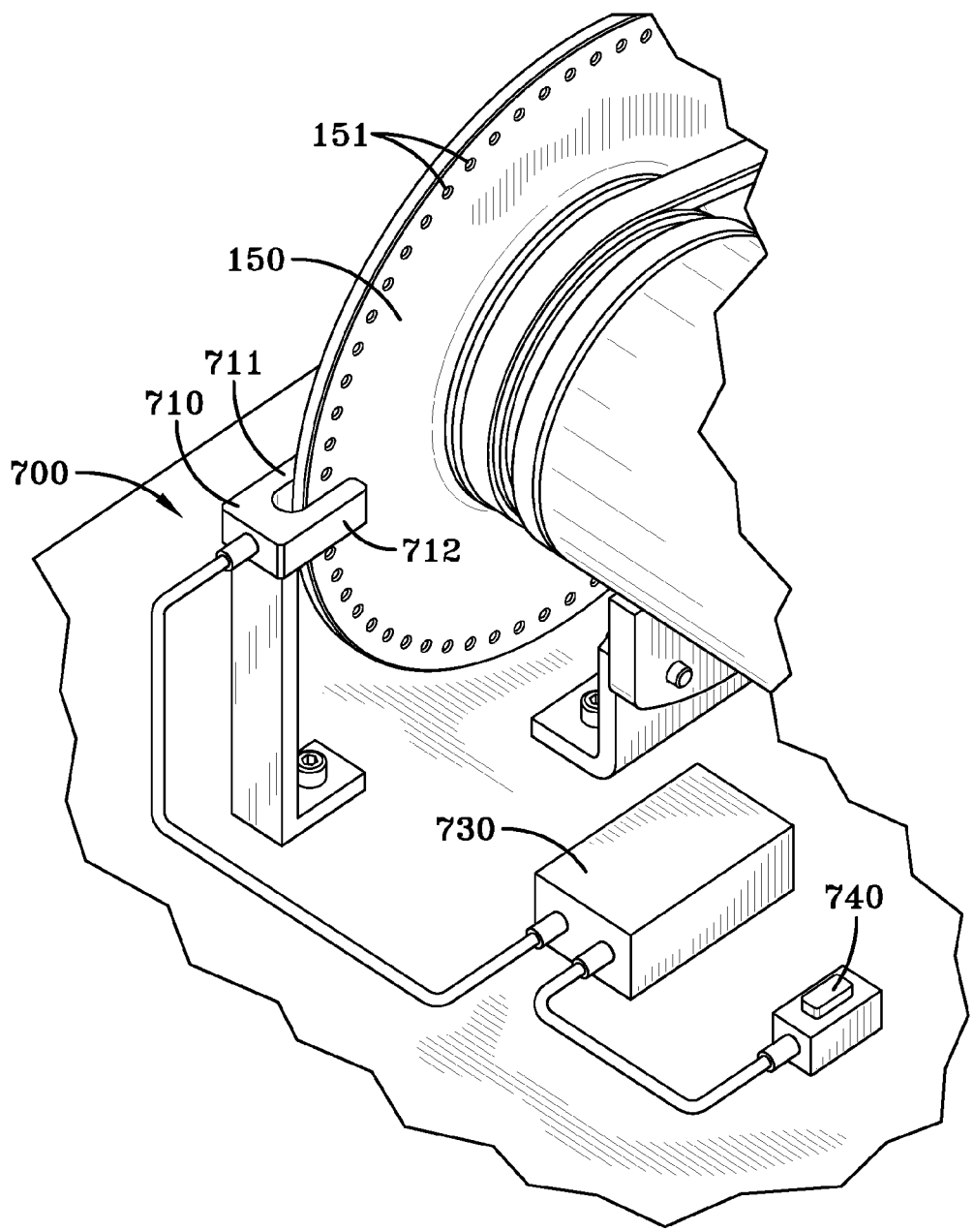

FIG. 3 a side view of the rotary indexer, digital displacement indicator, bearing, and shaft in operation;

FIG. 4 is a truncated perspective view of the rotary indexer and optical interrupter; and FIG. 5 is side view of the rotating mechanism.

DESCRIPTION

Figure 1:
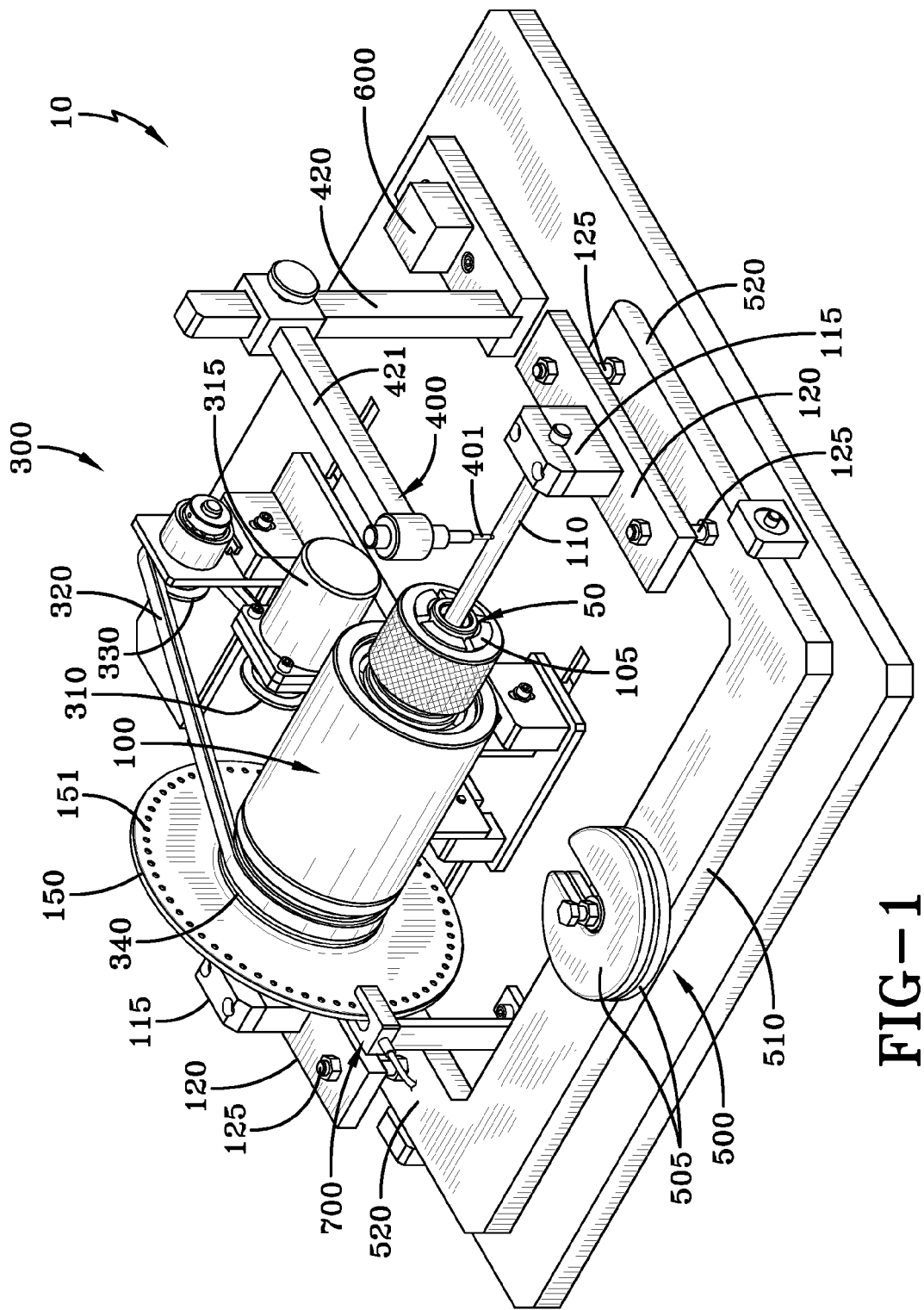

The preferred embodiments of the present invention are illustrated by way of example below and in FIGS. 1-5. As shown in FIG. 1, the apparatus 10 for mapping liner wear of a bearing 50 around the circumference of the bearing 50 includes a rotary indexer 100 that can hold the bearing 50, a shaft 110, a force applying mechanism 500, a rotating mechanism 300, a digital displacement indicator 400, and a recorder 600. As shown in FIGS. 2A-D, the bearing 50 has a ball 51, a liner 52, and an outer ring 53. The outer ring 53 may also be referred to as a "race." The liner 52 may be composed of resin, polytetrafluoroethylene (PTFE) fiber, composite material, or any material that can lubricate the bearing 50. The ball 51 is disposed within the outer ring 53, while the bearing liner 52 is attached to the inner circumference of the outer ring 53. The rotary indexer 100 can hold the outer ring 53 of the bearing 50. The shaft 110 is able to be inserted through a bore 54 of the ball 51 (the bore 54 is shown in FIGS. 2A and 2B). The shaft 110 is fixed at both ends such that the shaft 110 is unable to rotate. The force applying mechanism 500 communicates with the shaft 110 such that the force applying mechanism 500 applies constant upward radial force on the shaft 110, which in turn, applies upward force on the ball 51 such that the force causes the ball 51 to press against the liner 52. The rotating mechanism 300 can rotate the rotary indexer 100, and the rotary indexer 100 communicates with the outer ring 53 such that the rotary indexer 100 can rotate the outer ring 53. The digital displacement indicator 400 determines displacement of the ball 51 from the vertical motion of the shaft 110. The recorder 600 is for recording the displacement of the ball 51 at various rotational positions of the outer ring 53 and analyzing the displacement to determine liner wear at rotational positions of the outer ring 53.

In the description of the present invention, the invention will be discussed in a military aircraft environment; however, this invention can be utilized for any type of application that requires bearing liner wear diagnosis.

A rotary indexer 100 may be defined, but without limitation, as a fixture which holds a work piece (a bearing 50) and allows rotation of the work piece to align the work piece with discrete angular positions demarcated on the fixture. In one of the preferred embodiments, as shown in FIGS. 1 and 3, the bearing 50 being tested is held in the rotary indexer 100 by means of a collet 105. The collet 105 communicates with the outer ring 53 such that the outer ring 53 and the liner 52 can be rotated by the rotary indexer 100. The shaft 110 is inserted through the bearing 50, specifically through a bore in the ball 51. Each end of the shaft 110 is attached to corresponding shaft supports 115. The shaft supports 115 are connected to the shaft 110, such that the shaft 110 cannot rotationally move. Each shaft support 115 is attached to a mounting plate 120. The shaft supports 115 are positioned equidistantly around the bearing 50 such that the resultant upwards radial force on the bearing 50 acts on the center of its width. As shown in FIG. 1, the rotary indexer 100 may include a rotary encoder wheel 150 for providing discrete rotational positions to be monitored by the recorder 600. The rotary encoder wheel 150 may include holes 151 interspaced along its circumference, which are detectable by an optical interrupter 700. An optical interrupter 700 may be defined, but without limitation, as any paired light source and light sensor. In one of the preferred embodiments there are one hundred and eighty (180) holes on the rotary encoder wheel 150. The preferred embodiment of the optical interrupter 700, shown in FIG. 4, includes a yoke 710 with a first yoke arm 711 and a second yoke arm 712. The two yoke arms 711 and 712 form a u-shape that envelopes the rotary encoder wheel 150 and still allows it to spin. The yoke 710 communicates with a light analyzing microcontroller 730 which in turn may communicate with the main microcontroller 740.

As shown in FIG. 1, the force applying mechanism 500 may be a weight system. The weight system may include a weight or weights 505 for applying force, a weight bar 510, and two lever arms 520. The weight(s) 505 may be disposed at about the center of the weight bar 510, while the lever arms 520 are disposed on opposite ends of the weight bar 510. Each lever arm 520 communicates to a corresponding mounting plate 120 via mounting plate bolts 125 such that the force applying mechanism 500 (or weight mechanism) can apply an upward force on the shaft 110. However, any type of force applying system capable of applying a constant (not changing with varying bearing displacement or time) upward force during the test may be utilized.

A digital displacement indicator 400 may be defined, but without limitation, as a device which measures relative linear position and relays and/or displays the measurement digitally. As shown in FIGS. 1 and 3, the digital displacement indicator 400 may include a stem 401 and may be positioned such that the stem rests on top of the shaft 110 and is lowered to near the middle of its stroke. The digital displacement indicator 400 may be attached to a displacement indicator stand 420 via a displacement indicator lever 421.

The recorder 600 may be in the form of a microcontroller. In such an embodiment, the microcontroller also controls the rotating mechanism, and provides power to and monitors the state of the optical interrupter. The light analyzing microcontroller 730 and main microcontroller 740 may all be one microcontroller.

The rotating mechanism 300 rotates the rotary indexer 100 and the outer ring 53, which in turn rotates the liner 52. As shown in FIGS. 1 and 5, the rotating mechanism 300 may include a drive pulley 310 powered by a motor 315, which moves a belt 320 tensioned by a tensioner idler pulley 330, which rotates a driven pulley 340 attached to the rotary indexer 100. The driven pulley 340 rotates the rotary indexer 100 at a desired rotational speed.

In operation, as the rotary indexer 100 rotates, the optical interrupter 700 is interrupted by gaps between holes on the rotary encoder wheel 150. As the voltage from the optical interrupter 700 changes between its interrupted and non-interrupted state, the light analyzing microcontroller 730 triggers an interrupt in the main microcontroller 740, such that three hundred and sixty (360) interrupts are triggered for one rotation of the rotary indexer 100. Each time an interrupt is triggered, the main microcontroller 740 takes a measurement from the digital displacement indicator 400, and the measurement is stored in an array. When one rotation of the rotary indexer 100 has completed, the main microcontroller 740 stops the motor and analyzes the data in order to determine a baseline non-wear value and the magnitude of each measurement relative to its value. The main microcontroller 740 can then save the analyzed data, display the analyzed data as a wear map, and rotate the bearing to align the digital indicator stem 401 with any desired feature of interest. The main microcontroller 740 also compensates for any free play in the system not caused by liner wear. It compensates by referencing saved calibration data gathered when running the test with a solid metallic bushing in place of the lined bearing, and applying that displacement data to the wear analysis of subsequent lined bearing tests.

In operation, the rotary indexer 100 is rotated to its zero degree position, and the digital displacement indicator is zeroed at the beginning of each test.

When introducing elements of the present invention or the preferred embodiment(s) thereof, the articles "a," "an," "the," and "said" are intended to mean there are one or more of the elements. The terms "comprising," "including," and "having" are intended to be inclusive and mean that there may be additional elements other than the listed elements.

Although the present invention has been described in considerable detail with reference to certain preferred embodiments thereof, other embodiments are possible. Therefore, the spirit and scope of the appended claims should not be limited to the description of the preferred embodiment(s) contained herein.

What is claimed is:

1. An apparatus for mapping liner wear of a bearing around a circumference of the bearing, the bearing having a ball, a liner, and an outer ring, the apparatus comprising:
   a rotary indexer that can hold the bearing, the ball disposed within the outer ring, the outer ring having an inner circumference, the bearing liner attached to the inner circumference of the outer ring;
   a shaft, the shaft being able to be inserted through a bore of the ball, the shaft is fixed at both ends such that the shaft is unable to rotate;
   a force applying mechanism communicating with the shaft such that the force applying mechanism applies constant upward radial force on the shaft which applies upward force on the ball such that the force applied by the shaft causes the ball to press against the bearing liner;
   a rotating mechanism that can rotate the rotary indexer, the rotary indexer communicating with the outer ring such that the rotary indexer can rotate the outer ring;
   a digital displacement indicator for determining displacement of the ball from a vertical motion of the shaft; and,
   a recorder for recording the displacement of the ball at various rotational positions of the outer ring and analyzing the displacement to determine liner wear at rotational positions of the outer ring.

* * * * *